(12) United States Patent
Koers

(10) Patent No.: US 11,767,542 B2
(45) Date of Patent: Sep. 26, 2023

(54) METHOD FOR REMOVAL OF HARMFUL SULPHUROUS COMPOUNDS FROM GAS MIXTURES

(71) Applicant: Bonno Koers, Doesburg (NL)

(72) Inventor: Bonno Koers, Doesburg (NL)

( * ) Notice: Subject to any disclaimer, the term of this patent is extended or adjusted under 35 U.S.C. 154(b) by 542 days.

(21) Appl. No.: 16/723,661

(22) Filed: Dec. 20, 2019

(65) Prior Publication Data

US 2020/0199629 A1    Jun. 25, 2020

(30) Foreign Application Priority Data

Dec. 24, 2018  (NL) .................................... 2022310

(51) Int. Cl.
  *C12P 5/02* (2006.01)
  *C12P 11/00* (2006.01)
  *C12P 13/00* (2006.01)

(52) U.S. Cl.
  CPC ............. *C12P 5/023* (2013.01); *C12P 11/00* (2013.01); *C12P 13/008* (2013.01)

(58) Field of Classification Search
  CPC .......... C12P 5/023; C12P 11/00; C12P 13/008
  See application file for complete search history.

(56) References Cited

U.S. PATENT DOCUMENTS

| | | | |
|---|---|---|---|
| 2005/0109697 A1* | 5/2005 | Olivier | C02F 3/34 210/615 |
| 2010/0089818 A1 | 4/2010 | Koers | 210/488 |
| 2016/0038873 A1 | 2/2016 | Matheis | B01D 53/85 |

FOREIGN PATENT DOCUMENTS

| | | | |
|---|---|---|---|
| CA | 2216461 | 10/2006 | ............. B01D 53/52 |
| EP | 2767584 | 8/2014 | ............. C12M 1/00 |
| EP | 3366764 | 8/2018 | ............ C12M 1/107 |
| EP | 3395429 | 10/2018 | ............. B01D 53/85 |
| NL | 2014997 | 1/2017 | ............. B01D 53/52 |
| PL | 230394 | 10/2018 | ............. B01D 53/52 |

OTHER PUBLICATIONS

Dutch Search Report and Written Opinion issued in application No. 2022310, dated Dec. 24, 2018 (10 pgs).

\* cited by examiner

*Primary Examiner* — David W Berke-Schlessel
*Assistant Examiner* — Trent R Clarke
(74) *Attorney, Agent, or Firm* — HAYES SOLOWAY P.C.

(57) ABSTRACT

Waste gas mixtures produced and used in industry may contain harmful sulphurous compounds. The present disclosure provides a method for treatment of gas mixtures contaminated with harmful sulphurous compounds by using microorganisms capable of degrading said harmful sulphurous compounds which involves controlling nitrate levels in the medium in which microbiological conversion of harmful sulphurous compounds takes place at high levels.

15 Claims, 2 Drawing Sheets

METHOD FOR REMOVAL OF HARMFUL SULPHUROUS COMPOUNDS FROM GAS MIXTURES

FIELD OF THE INVENTION

The present invention relates to a method for treatment of gas mixtures contaminated with harmful sulphurous compounds.

BACKGROUND OF THE INVENTION

Waste gas mixtures produced and used in industry may contain harmful sulphurous compounds. For instance, waste gas streams often contain $H_2S$, $SO_2$ and/or $CS_2$. These sulfur compounds are very harmful to the environment and human health. In general they generate an unpleasant smell and even at very low concentrations it can be life threatening. Moreover, they can be detrimental to combustion engines. Apart from that, $H_2S$ is in the combustion process converted to sulphur oxides (SOx), which are also harmful to the environment and human health. Also $CS_2$ is highly explosive, toxic and can lead to acute and chronic forms of poisoning.

There is a continuous need in industry for improved methods and apparatuses which remove harmful sulphurous compounds from gas mixtures.

DESCRIPTION OF THE INVENTION

The present invention relates to a method for treatment of gas mixtures contaminated with harmful sulphurous compounds by using microorganisms capable of degrading said harmful sulphurous compounds. Apart from said harmful sulphurous compounds, such gas mixtures often contain compounds which are inflammable in the presence of oxygen. Therefore methods for treatment of gas mixtures contaminated with harmful sulphurous compounds often need to be performed under anaerobic conditions at least until the risk of ignitions of said inflammable compounds is eliminated.

Anaerobic conversion of harmful sulphurous compounds by microorganisms in bioreactors produces a number of products including sticky sulphur. As bioreactors for use in gas cleansing in general make use of filters, onto which microorganisms are present in biofilms, an increased amount of sticky sulphur may lead to clogging of the system used for the gas cleaning method. This will limit the life time of an apparatus used for such method. In previous Dutch patent application 2014997 of the present inventor a method was described for treating a raw gas mixture which contains hydrogen sulphide, comprising introducing a stream of a raw gas mixture containing hydrogen sulphide and a stream of an aqueous slurry comprising anaerobic and aerobic micro-organisms into a first unit, contacting in said first unit said raw gas mixture with said slurry under anaerobic conditions, wherein upon contacting said raw gas mixture with said slurry at least part of the hydrogen sulphide is dissolved and converted to other sulphurous compounds in the slurry such that a product stream comprising lower hydrogen sulphide content compared to the raw gas mixture is obtained, passing said slurry from the first unit to a second unit wherein said slurry is treated by exposure to aerobic conditions so as to effect aerobic conversion of remaining $H_2S$ or other sulphurous compounds dissolved in the slurry to sulphuric acid; and recycling the major part of said slurry from the second unit to the first unit. This method strongly reduced the problem of clogging of sticky sulphur by following the anaerobic step directly with an anaerobic step in which oxidation to sulfuric acid takes place. However the inventor has considered that there is room for improvement, in particular in relation to the efficiency, timewise but also with regard to the materials used.

The present invention relates to a method for treating a raw gas mixture which contains harmful sulphurous compounds, comprising i) introducing into a first unit: a raw gas mixture containing harmful sulphurous compounds, and an acidic aqueous medium containing nitrate; ii) contacting in said first unit said raw gas mixture with micro-organisms capable of degrading said harmful sulphurous compounds in said aqueous medium; iii) allowing, under anaerobic conditions, said micro-organisms to metabolize in said aqueous medium at least part of said harmful sulphurous compounds to $H_2SO_4$ and to metabolize at least part of said nitrate such that that a gas product comprising a lower content of harmful sulphurous compounds compared to the raw gas mixture is obtained; and iv) discharging aqueous medium containing $H_2SO_4$ and said gas product from said first unit; wherein, in the acidic aqueous medium introduced into said first unit, the nitrate level is controlled at a level which is sufficient to allow conversion of at least part of said harmful sulphurous compounds to $H_2SO_4$ under said anaerobic conditions.

The invention is based on the observation that high levels of nitrate in an anaerobic bioreactor lead to full conversion of harmful sulphurous compounds to $H_2SO_4$. The inventor has namely surprisingly found that controlling the nitrate in the medium in which microbiological conversion of harmful sulphurous compounds takes place at high levels lead to full conversion to the soluble $H_2SO_4$. Thus, in the first unit said raw gas mixture containing harmful sulphurous compounds is contacted with said aqueous medium to effect that harmful sulphurous compounds are at least partially, but preferably completely, dissolved and converted into sulfuric acid in the medium such that a gaseous product comprising a lower concentration (preferably fully depleted) of harmful sulphurous compounds is obtained, which can be discharged from the first unit, and a liquid product of said aqueous medium which contains the produced sulfuric acid. This makes it possible to eliminate harmful sulphurous compounds under anaerobic conditions in a single bioreactor unit.

It is possible that in the first unit, a first step takes place wherein said raw gas mixture containing harmful sulphurous compounds is contacted with said aqueous medium by means of a continuous flow of said medium to effect that the harmful sulphurous compounds are at least partially dissolved and converted to sulfuric acid in the medium such that a gaseous product stream comprising lower amounts of harmful sulphurous compounds is obtained and that subsequently a second step (a polishing step) takes place in which said product stream is further washed by intermittently spraying the product stream with water takes place. It is preferred that washing of the product stream takes place with water, preferably potable water. The inventor has observed however that with the method of the present invention, such a polishing step is not necessary anymore. Nevertheless, in case a polishing step is applied, it is preferred that in first unit the raw gas mixture is washed first by means of said medium in a first chamber (washing chamber). Then, in a second anaerobic step a polishing step will take out the remaining harmful sulphurous compounds from the product gas to further purify the product. This second anaerobic step may take place in a second chamber by intermittently spraying the product stream with water, preferably potable water and results in a cleaned up product stream.

Although the inventor does not wish to be bound by theory, it is believed that under these anaerobic conditions the excess of nitrate makes it possible that nitrate functions as an oxidizing agent, thus allowing the oxidation reaction of harmful sulphurous compounds to $H_2SO_4$ under the formation of nitrite ($NO_2^-$) For instance if the harmful sulphurous compound is $H_2S$ the following reaction may take place:

$$5NO_3^- + H_2S \rightarrow 5NO_2^- + H_2SO_4 + H_2O$$

The method of the invention is carried out under highly acid conditions, preferably at a pH below 2, even more preferably below 1, such as at a pH of 0.7. For this purpose it is preferred that the pH the acidic aqueous medium containing nitrate introduce in the first unit is maintained below 2, even more preferably below 1, such as at a pH of 0.7. Because of this low pH the harmful sulphurous compounds, such as $H_2S$, are dissolved well and conversion is enhanced. Further because of the low pH growth of biomass of the autotropic organisms metabolizing the harmful sulphurous compounds will be limited, resulting in a minimal risk of clogging of the bioreactor.

More importantly, the inventor has observed that carrying out the method of the invention under highly acid conditions, preferably at a pH below 2 or even below 1 makes it possible to regenerate nitrate from the nitrite produced in the oxidation reaction of the harmful sulphurous compounds. An important further advantage of this is that the method of the invention in principle does not require additional chemicals to allow the oxidation from nitrite to nitrate. Although the inventor does not wish to be bound by theory, it is believed that under these highly acid conditions make the nitrite less stable and therefore susceptible to oxidation back to nitrate under aerobic conditions. Therefore, in a preferred embodiment of the method of the invention step iii) comprises allowing said micro-organisms to convert in said aqueous medium at least part of said harmful sulphurous compounds to $H_2SO_4$ and at least part of said nitrate into nitrite to obtain an aqueous medium containing $H_2SO_4$ and nitrite; and also comprises the steps of v) passing said aqueous medium containing $H_2SO_4$ and nitrite from said first unit to a second unit, in which, under aerobic conditions, nitrate is regenerated by an oxidation reaction of nitrite to nitrate to obtain an aqueous medium containing $H_2SO_4$ and nitrate; and vi) recycling at least part of said aqueous medium containing $H_2SO_4$ and nitrate from said second unit back to said first unit to function as said acidic aqueous medium containing nitrate of step i). This embodiment has the advantage that the nitrate levels upon entry of the medium into the first unit can be controlled at high levels without the need for continuous supply of fresh nitrate from an outside source, which saves considerable costs and effort. Although the inventor does not wish to be bound by theory, it is believed that under the highly acidic conditions of the method of the invention, such as below pH 1, the nitrite is very unstable so that chemical oxidation to nitrate takes place because oxygen is freely available in the second, aerobic unit. However, as the second unit in general also contains microorganisms in order to convert any sulphurous compounds that were not converted in the first unit, a role for these microorganisms in the oxidation of nitrite to nitrate cannot be excluded. Even though this embodiment of the present invention requires a second reactor, this can be a reactor of limited size, because require a large second aerobic bioreactor is not required. The nitrate regeneration namely can take place in a reactor with only a fraction of the size of an aerobic bioreactor for converting sulphur containing products to sulfuric acid, for instance as described in Dutch patent application 2014997 of the present inventor. Moreover, recycling the $H_2SO_4$ back into the first unit helps to maintain the highly acidic environment required for carrying out the method of the invention. It also allows a continuous flow of medium through the units ensuring a stable population of the required micro-organisms. In this respect the method provides the possibility of a continuous process.

To maintain the sulfuric acid concentration so that it will not turn into a too concentrated acid and that it will still be capable of dissolving harmful sulphurous compounds, a small percentage of the flow is refreshed with potable water, optionally with fresh nitrate. It is preferred that the sulphuric acid in the slurry from the second unit is brought to a concentration of between 2 and 8% (by weight), preferably approximately 6.5% (by weight) before being introduced into the first unit. Depending on the conditions higher percentages of sulphuric acid in the slurry entering the first unit may also be acceptable.

The required levels of nitrate can be determined by increasing in a start-up phase the level of nitrate until a level at which sufficiently low levels of sticky sulphur are formed in the first unit. It is preferred that most of the harmful sulphurous compounds are fully converted to $H_2SO_4$ in the first unit. It is therefore preferred that in the acidic aqueous medium introduced into said first unit, nitrate is controlled at a level which is sufficient to allow conversion of essentially all harmful sulphurous compounds to $H_2SO_4$ under said anaerobic conditions. With essentially all is meant at least 90 mol %, preferably at least 95 mol %, most preferably at least 99 mol % with respect to entry levels. These levels can be determined for instance by increasing in a start-up phase the level of nitrate until a level at which essentially no sticky sulphur is formed in the first unit or until a level is obtained at which a stable and high rate of sulphuric acid is produced in the anaerobic bioreactor.

Any sulphurous compounds which are not converted into sulphuric acid in the first unit can passed from the first unit to the second unit together with the stream of aqueous medium containing sulphuric acid and nitrite. There, any remaining sulphurous compounds, for instance elementary sulphur, can be converted under aerobic conditions by oxidation to sulphuric acid to complete the elimination of any undesired and harmful sulphurous compounds.

Common harmful sulphuric compounds present in raw gas mixtures encompass for instance compounds selected from the group of $H_2S$, $CS_2$, $SO_x$. An example of $SO_x$ is $SO_2$.

The inventor has observed in practice that the method of the invention is in particular suitable for cleaning gas mixtures from $H_2S$ and/or $CS_2$ and excellent results were obtained in this respect. Raw gas mixtures containing $H_2S$ and/or $CS_2$ are common products of industrial processes. Optimal results regarding the conversion of these compounds were found if the nitrate was controlled at a level in a molar ratio with respect to the portion atomic sulphur in said $H_2S$ and/or $CS_2$ introduced into said first unit of at least 5:1. In other words, for each mole of $H_2S$ introduced in the first unit 5 moles of nitrate should be present and for each mole of $CS_2$ introduced in the first unit 10 moles of nitrate should be introduced in the first unit. Best results were obtained if at least 1.3 times higher levels of nitrate were applied, i.e. a level of nitrate in a ratio with respect to the portion atomic sulphur in said $H_2S$ and/or $CS_2$ introduced into said first unit of at least 6.5:1.

Therefore in one embodiment of the method of the invention said harmful sulphurous compounds are $H_2S$ and/or $CS_2$ and in the acidic aqueous medium introduced into said first unit, nitrate is controlled present in a molar ratio with respect to the portion atomic sulphur in said $H_2S$ and/or $CS_2$ introduced into said first unit of at least 5:1, preferably at least 6.5:1. In a particular embodiment said raw gas mixture contains $H_2S$ and in step iii) said micro-organisms metabolize in said acidic aqueous medium under anaerobic conditions $H_2S$ to $H_2SO_4$, while in the acidic aqueous medium introduced into said first unit, nitrate is controlled to be present in a molar ratio with respect to the portion atomic sulphur in said $H_2S$ introduced into said first unit of at least 5:1, preferably at least 6.5:1. In another particular embodiment said raw gas mixture contains $CS_2$ and in step iii) said micro-organisms metabolize in said acidic aqueous medium under anaerobic conditions $CS_2$ to $H_2SO_4$, while in the acidic aqueous medium introduced into said first unit, nitrate is controlled to be present in a molar ratio with respect to the portion atomic sulphur in said $CS_2$ introduced into said first unit of at least 5:1, preferably at least 6.5:1. In another particular embodiment said raw gas mixture introduced into said first unit contains both $H_2S$ and $C_2S$ and in step iii) said micro-organisms metabolize in said acidic aqueous medium under anaerobic conditions $H_2S$ and $C_2S$ to $H_2SO_4$, while in the acidic aqueous medium introduced into said first unit, nitrate is controlled to be present in a molar ratio with respect to the portion atomic sulphur in said $H_2S$ and $C_2S$ introduced into said first unit of at least 5:1, preferably at least 6.5:1.

In the method according to the invention the raw gas mixture may be produced in any industrial process leading to the production of harmful sulphurous compounds. For instance the raw gas mixture may be selected from the group comprising boiler gas, landfill gas, flare gas and biogas. The raw gas mixture is passed from its site of production to the first unit to be treated in accordance with the method of the invention. The first unit in the context of the invention will therefore be downstream of the place or device of production of said raw gas mixture.

The raw gas mixture may for instance be any gas comprising $H_2S$, i.e. any sour gas. The method of the invention may therefore be applicable to any sour gas. In one preferred embodiment the raw gas mixture is biogas. The term biogas typically refers to a mixture of different gases which are produced by the digestion of organic matter in the absence of oxygen. The method of the invention in this case thus takes place after this digestion and is meant to clean the biogas from harmful sulphurous compounds after its production. This means that the first unit in this case will be positioned downstream of a digester that digests organic matter for production of biogas. Sources for biogas can be raw materials such as agricultural waste, manure, municipal waste, plant material, sewage or petrochemical waste.

As the method according to the invention enables degradation of harmful sulphurous compounds to sulfuric acid in a single stage under anaerobic conditions, there is no risk of fire if the raw gas mixture introduced into the first unit contains inflammable material. Therefore, in one embodiment the raw gas mixture may comprise inflammable material. An inflammable material that is often present in industrial gases is methane ($CH_4$). Therefore, the inflammable material may comprise $CH_4$. CH4 is for instance a component of biogas. Biogas is a gas mixture that can be produced by anaerobic digestion with anaerobic bacteria, which break down the organic carbon in the raw materials to a biogas which is mainly comprised of methane ($CH_4$) but which contains contaminants such as carbon dioxide ($CO_2$) nitrogen ($N_2$) and hydrogen sulphide ($H_2S$). Further, methane often produced at by-product of industrial processes, for instance in oil industry, wherein operators will often vent or flare the gas mixture produced. This gas is commonly called flare gas. It is common that flare gases are contaminated with $H_2S$. Flare gases commonly also contain methane. While the harmful sulphurous compounds dissolve in the aqueous medium, the methane remains in gaseous form and can as such be easily separated and discharged from the first unit in the form of a product gas containing a very low level of harmful sulphurous compounds (if still present at all) and a substantial level of methane. In this respect it is preferred that in the first unit, a first step takes place wherein a raw gas mixture containing methane and hydrogen sulphide is contacted with said medium to effect that harmful sulphurous compounds (e.g. $H_2S$ or $CS_2$) are at least partially dissolved and converted to sulfuric acid in the slurry such that a product stream comprising methane and lower concentration of said harmful sulphurous compounds is obtained and that subsequently a second step takes place in which said product stream is further washed by intermittently spraying the product stream with water in order to purify the methane.

This methane can be combusted or oxidized with oxygen to release energy, for example for use in gas engines.

The aqueous medium introduced into the first unit may be in the form of aqueous slurry comprising anaerobic and optionally also aerobic micro-organisms, such as bacteria or mixtures of bacteria which are known in the art for purposes of removing harmful sulphurous compounds, such as $H_2S$, $CS_2$ and $SO_x$ from gases, liquids or fluids. Bacterial cultures for aerobic and/or anaerobic conversion of harmful sulphurous compounds are known and available in the art. Such bacteria may for example include bacteria belonging to the *Thiobacillus* genus. Apart for nitrate, the slurry may comprise additional food sources for the micro-organisms or other supplements. The method of the invention allows the use of said slurry without the need for harmful chemicals.

The first and second units are suitably in the form of bioreactors. In the first unit preferably structures are provided which facilitate diffusion between the aqueous medium and raw gas mixture introduced into the first unit. These structures are preferably synthetic structures. Structures that may be suitable for these purposes are known in the art and may be filter packages made of plastics such as HDPE or polypropylene. Examples of a suitable filter packages are described in patent applications US2010/0089818 and EP3395429. Such structures are commonly referred to in the art as structured packing. The micro-organisms used in the method of the invention may perform their activity floating in the medium, but can also be present on the structures in biofilms, where they can also perform their activity of degrading harmful sulphurous compounds in accordance with the method of the invention to sulphuric acid. In accordance, the first unit may in a preferred embodiment relate to a biotrickling filter. Accordingly, the method of the invention preferably at least comprises a biotrickling process in the first unit. In case of biogas, the first unit will therefore be placed downstream of a digester that produces biogas from organic matter. In general in an initial stage a slurry with microorganisms is passed continuously through the first unit which in time results in biofilm formation. This slurry is then circulated through the reactors and anaerobic bacteria will settle in the first unit as biofilms for anaerobic conversion of harmful sulphurous compounds to $H_2SO_4$ and aerobic bacteria will settle in the second unit as biofilms for the aerobic conversion of any remaining unconverted sulphurous compounds to $H_2SO_4$ and possibly contributing in the regeneration of nitrate from nitrite. After a certain start up time microbiological cultures will perform stably, ensuring a continuous conversion of harmful sulphurous compounds.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present disclosure. Moreover, in the drawings, like reference numbers designate corresponding parts throughout the several views.

DETAILED DESCRIPTION

Figure 1:
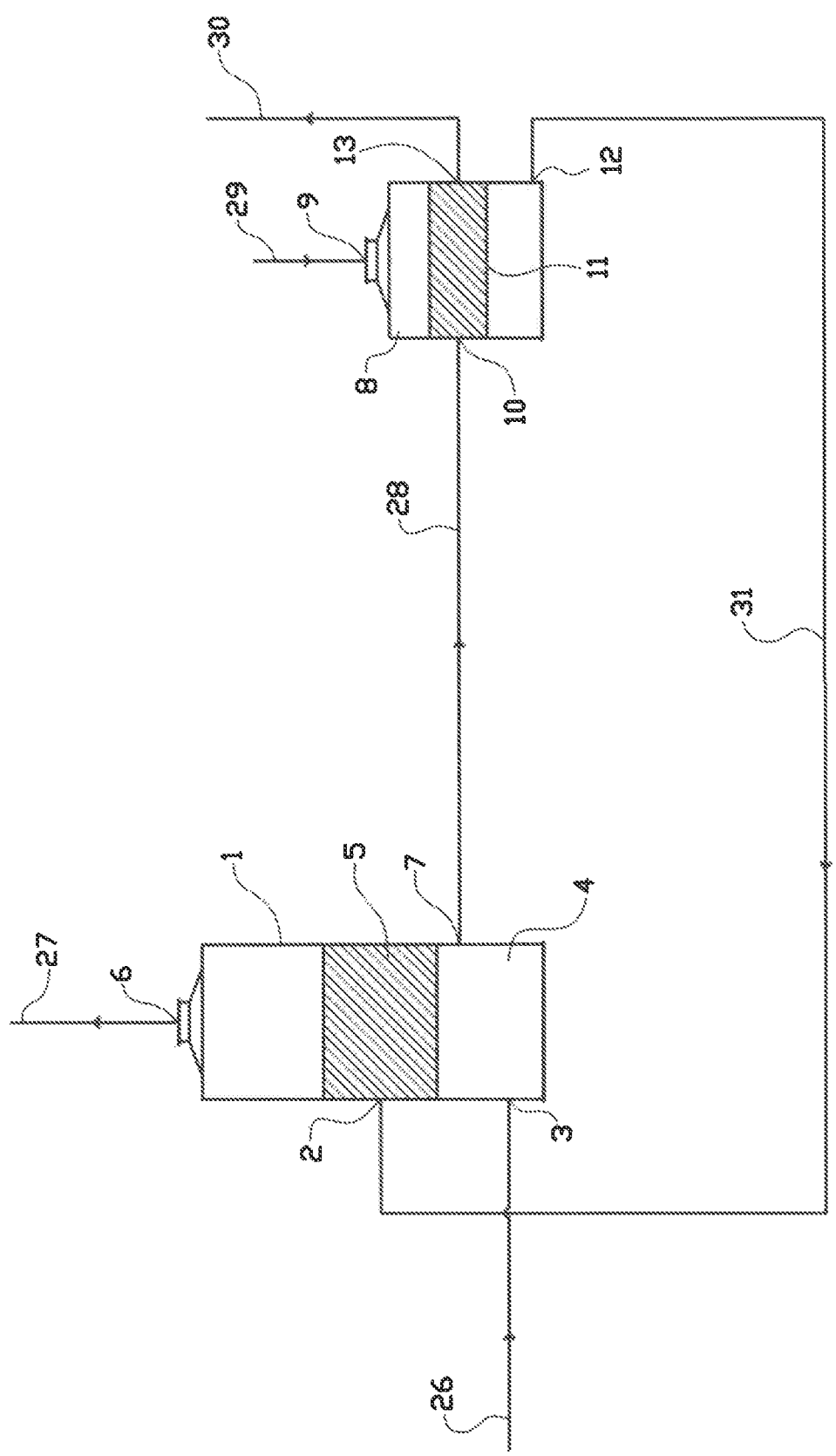
FIG. 1 is a schematic representation of the method of the present invention.

The method of the invention can be carried out by means of an apparatus as shewn in FIG. 1. FIG. 1 shows an schematic representation of an apparatus for treating a raw gas mixture which contains harmful sulphurous compounds, comprising a first unit (1), which when in operation is an anaerobic unit. This first unit comprises an inlet (2) for the acidic aqueous medium, an inlet (3) for receiving said raw gas mixture (which in a particular preferred embodiment contains methane and $H_2S$); a first chamber (4) in connection with said inlet (2) for receiving said aqueous medium and said inlet (3) for receiving said raw gas mixture, said first chamber comprising a structure (5) for facilitating diffusion between said medium and said raw gas mixture, so as to enable at least partial dissolving harmful sulphurous compounds and at least partial converting harmful sulphurous compounds to sulfuric acid in the medium such that a gas product comprising lower content of harmful sulfuric compounds compared to the raw gas mixture (in a particular preferred embodiment a product stream comprising methane and lower $H_2S$ content compared to the raw gas mixture) is obtained; an outlet (6) for passing out said gas product, and an outlet (7) for said medium via which the medium can be passed to a second unit which is an aerobic unit under operational conditions. Microorganisms may be comprised in the acid medium introduced via inlet (2) and/or be present as biofilms on said structure (5).

The apparatus of the invention further comprises a second unit (8) comprising an inlet (9) for an oxygen containing gas (such as air) in order to allow aerobic conditions in the second unit; an inlet (10) in connection with said outlet (7) for said medium of the first unit (1) for receiving slurry from said first unit; a structure (11) for facilitating diffusion of said slurry with the oxygen containing gas so as to allow aerobic conversion of any remaining nitrite dissolved in the slurry back to nitrate; an outlet (12) for said medium; and a gas outlet (13) in connection with the surroundings to allow release of gas. The units, outlets and inlets and other elements of the apparatus are interconnected or connected with the surroundings by connection means (26, 27, 23, 29, 30, 31)

In the apparatus said cutlet (12) for said medium of the second unit is in connection with the inlet (2) for medium of the first unit so as to enable recycling of at least a part of said medium from the second unit to the first unit in order to provide nitrate to the first unit (1). The recycling of medium from the second unit to the first unit provides an anaerobic and acid environment which increases dissolving and conversion of harmful sulphurous compounds, such as $H_2S$, in the slurry. In particular when the gas mixture contains methane and $H_2S$ the recycling of the major part of the slurry from the second unit to the first unit provides an anaerobic and acid environment which reduces biological loss of $CH_4$ to a minimum, while increasing $H_2S$ dissolving and conversion in the slurry.

The skilled person will understand that connections between the units, inlets, outlets can be provided by any connections means that enable a stream of gases, fluids or liquid such as tubings or pipes. Likewise the inlets and outlets of the apparatus can be provided with any suitable tubing or pipe that enables entry or exit of gases, fluids or liquids from chambers and/or units.

The apparatus preferably further comprises in the first unit a second chamber which is in connection with the first chamber, comprising a structure for facilitating diffusion of water and said product stream and a means for providing an intermittent flow of water into the second chamber so as to enable removing any residual harmful sulphurous compounds from the product stream from said first chamber. The incorporation of this element provides the opportunity of applying a step to "polish" the product stream, which in a preferred embodiment contains methane, from the first chamber to obtain a further cleaned up product stream.

The apparatus may suitably be provided with a blower to bring the right amount of ambient air into the second unit to allow for the full oxidation process of the anaerobic slurry from the first unit. Vents may also be added in the apparatus where gases need to be ventilated out of the apparatus.

The apparatus may be suitably provided with pumps to pump the gases, fluids or liquids to and from the respective compartments.

Exemplary Embodiment

In the following paragraph an exemplary embodiment of an apparatus which can be used for performing the method of the invention will be explained with reference to FIG. 2 in reference to an process in which a raw gas mixture comprising methane and $H_2S$ is cleaned.

Figure 2:
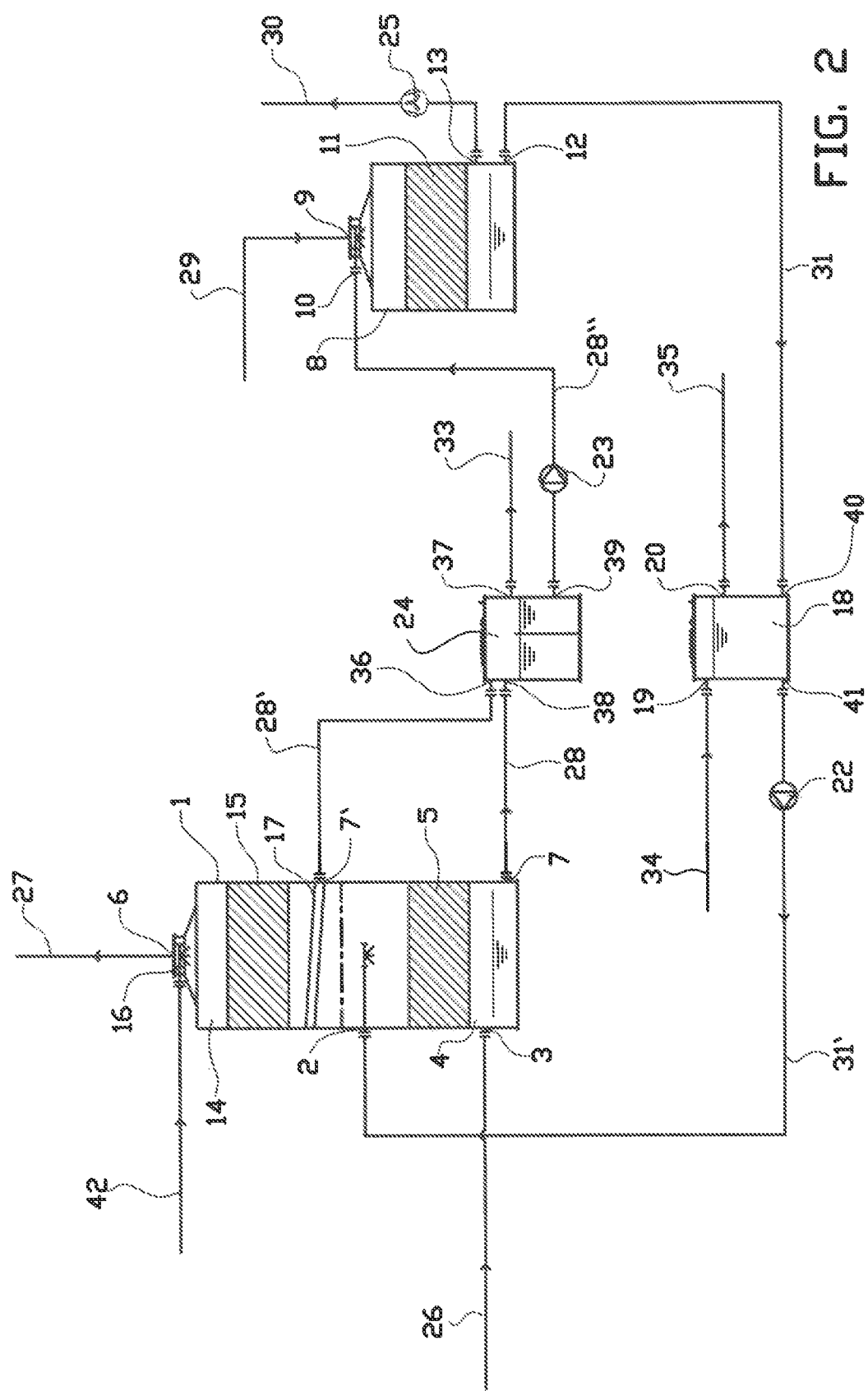
FIG. 2 depicts an apparatus for practicing the method of the present invention.

FIG. 2 shows an exemplary embodiment of the apparatus of the invention in which a raw gas mixture comprising methane and $H_2S$ is passed via piping (26) and inlet (3) into the first chamber (4) of a first unit (1). The first unit (3) also comprises an inlet (2) for receiving via piping (31, 31') an aqueous slurry comprising anaerobic and aerobic microorganisms. This slurry is introduced into the first chamber (4) in a strong and continuous flow. In the first chamber (4) synthetic and structured media (5) are installed which optimize diffusion between the raw gas mixture and the aqueous slurry and which allow for optimal exchange of components. In this treatment, at least part, but preferably most or even more preferably substantially ail of the $H_2S$ is absorbed or dissolved into the slurry and at least partially converted to other sulphurous compounds in the slurry. After this treatment the cleaned up gas is passed to a second chamber (14) which is situated above the first chamber. The slurry is passed out of the first chamber (4) via outlet (7) and piping (28). In the second chamber (14) the gas will be "polished" to take out remaining $H_2S$. The second chamber (14) also comprises a structure (15) for facilitating diffusion of the water and gas. In the second chamber any residual $H_2S$ is removed from product stream by intermittently spraying the product stream with water by means (16) via piping (42) for providing an intermittent flow of water. The purified methane gas is released from the first unit via outlet (6) and piping (27). The first and the second chamber (4, 14) are separated by a water collector (17) which allows washing said structure for facilitating diffusion, for instance by rinsing the structure with a caustic mixture. The water collector is configured such that flow of the methane containing gaseous product stream from the first to the second chamber is possible, for instance in the form of drain gutters. The first chamber (4) is connected via outlet (7) and piping 28 with inlet (36) of buffer tank (24). The second chamber (14) is connected (optionally via water collector (17)) via outlet (7') and piping (28') with inlet (36) of the buffer tank (24). In the buffer tank the anaerobic wash slurry which contains the converted products of the biological conversion from the second chambers, i.e. nitrite and sulfuric acid, is collected. The buffer tank can be connected via outlet (37) and piping (33) to a drain sump to allow draining of excess slurry. From the buffer tank (24) the slurry is passed via outlet (39) and piping (28") to a second unit (8). This unit is provided with an inlet (9) for supplying an oxygen containing gas via piping (29); an inlet (10) in connection via piping (28, 28', 28''') with said outlet of the first unit for receiving slurry from said first unit; a structure (11), preferably a synthetic structure, for facilitating diffusion of said slurry so as to allow aerobic conversion of nitrite to nitrate; an outlet (12) for said slurry; and a gas outlet (13) in connection with the surroundings via a pipe (30). In this pipe (30) a vent (25) may be connected to allow ventilation of gases. The outlet (14) for said slurry of the second unit is in connection with the inlet (2) for slurry of the first unit via piping (31, 31') so as to enable recycling of said slurry from the second unit (8) to the first unit (1). The apparatus of this embodiment further comprises a means (18) for replenishing the slurry with fresh water and nitrate in the slurry positioned via inlet (40) and outlet (41) in piping (31, 31') between the outlet (12) for said slurry of the second unit (8) and the inlet (2) for said slurry of the first unit (1). Means (18) may be connected to a water supply, wherein the water with a desired level of nitrate is present, via inlet (19) and piping (34) and a drain sump via outlet (20) and piping (35). Means (18) functions to enable control of the sulphuric acid and nitrate content in the slurry before it is recycled back the first unit (1). The apparatus is provided with pumps (22) and (23) to pump the gases, fluids or liquids to and from the respective compartments. The apparatus may also be provided with a blower to bring the right amount of oxygen containing gas (preferably ambient air) into the second unit (8) to allow for the full oxidation process of the anaerobic slurry from the first unit (1). It will be obvious that many changes can be made to the exemplary embodiment according to the invention in the paragraph above without being beyond the inventive idea as it is defined in the claims.

The invention claimed is:

1. A method for treating a raw gas mixture which contains harmful sulphurous compounds, comprising
   i) introducing into a first unit:
      a raw gas mixture containing harmful sulphurous compounds, and
      an acidic aqueous medium containing nitrate;
   ii) contacting in said first unit said raw gas mixture with micro-organisms capable of degrading said harmful sulphurous compounds in said aqueous medium;
   iii) passing said aqueous medium with said nitrate and said raw gas mixture through a synthetic structure comprising a biofilm of said micro-organisms for facilitating diffusion between said medium and said raw gas mixture, and allowing, under anaerobic conditions, said micro-organisms to metabolize in said aqueous medium at least part of said harmful sulphurous compounds to sulphuric acid ($H_2SO_4$) and to metabolize at least part of said nitrate into nitrite such that a gas product comprising a lower content of harmful sulphurous compounds compared to the raw gas mixture and an aqueous medium containing $H_2SO_4$ are obtained;
   iv) discharging aqueous medium containing $H_2SO_4$, said nitrite and said gas product from said first unit;
   wherein, in the acidic aqueous medium introduced into said first unit, the nitrate level is controlled at a level which is sufficient to allow conversion of at least part of said harmful sulphurous compounds to $H_2SO_4$ under said anaerobic conditions;
   v) passing said aqueous medium containing $H_2SO_4$ and nitrite from said first unit to a second unit in which, under aerobic conditions, nitrate is regenerated by an oxidation reaction of nitrite to nitrate to obtain an aqueous medium containing $H_2SO_4$ and nitrate; and
   vi) recycling at least part of said aqueous medium containing $H_2SO_4$ and nitrate from said second unit back to said first unit to function as said acidic aqueous medium containing nitrate of step i);
   wherein in said aqueous medium throughout the method the pH is maintained below 2.

2. The method according to claim 1, wherein, in the acidic aqueous medium introduced into said first unit, the nitrate level is controlled at a level which is sufficient to allow conversion of essentially all harmful sulphurous compounds to $H_2SO_4$ under said anaerobic conditions.

3. The method according to claim 1, wherein said harmful sulphurous compounds are $H_2S$ and/or $CS_2$, and wherein, in the acidic aqueous medium introduced into said first unit, the nitrate level introduced into said first unit is controlled to a molar ratio with respect to the portion atomic sulphur in said $H_2S$ and/or $CS_2$ introduced into said first unit of at least 5:1.

4. The method according to claim 1, wherein said raw gas mixture contains $H_2S$, and wherein in step iii) said micro-organisms metabolize in said acidic aqueous medium under anaerobic conditions $H_2S$ to $H_2SO_4$, and wherein, in the acidic aqueous medium introduced into said first unit, the nitrate level is controlled to a molar ratio with respect to the portion atomic sulphur in said $H_2S$ introduced into said first unit of at least 5:1.

5. The method according to claim 1, wherein said raw gas mixture contains $CS_2$, and wherein in step iii) said micro-organisms metabolize in said acidic aqueous medium under anaerobic conditions $CS_2$ to $H_2SO_4$, and wherein, in the acidic aqueous medium introduced into said first unit, the nitrate level is controlled to a molar ratio with respect to the portion atomic sulphur in said $CS_2$ introduced into said first unit of at least 5:1.

6. The method according to claim 1, wherein said raw gas mixture introduced into said first unit contains both $H_2S$ and $CS_2$, and wherein in step iii) said micro-organisms metabolize in said acidic aqueous medium under anaerobic conditions $H_2S$ and $CS_2$ to $H_2SO_4$, and wherein, in the acidic aqueous medium introduced into said first unit, the nitrate level is controlled to a molar ratio with respect to the portion atomic sulphur in said $H_2S$ and $CS_2$ introduced into said first unit of at least 5:1.

7. The method according to claim 3, wherein, in the acidic aqueous medium introduced into said first unit, said molar ratio is at least 6.5:1.

8. The method according to claim 1, wherein the pH of the acidic aqueous medium is less than 1.

9. The method according to claim 1, wherein the raw gas mixture is selected from the group comprising boiler gas, landfill gas, flare gas and biogas.

10. The method according to claim 1, wherein the raw gas mixture contains inflammable material.

11. The method according to claim 10, wherein the inflammable material comprises $CH_4$.

12. The method according to claim 9, wherein the raw gas mixture is biogas and wherein said first unit is provided downstream of a digester that produces biogas from organic matter.

13. The method according to claim 1, wherein said first unit is a biotrickling filter.

14. The method according to claim 2, wherein the raw gas mixture contains inflammable material.

15. The method according to claim 14, wherein the raw gas mixture contains $CH_4$.

* * * * *